United States Patent [19]

Frank

[11] 3,964,831

[45] June 22, 1976

[54] VISUAL COLOR COMPARATOR WITH INTEGRAL DUAL DIP CELLS

[75] Inventor: Gomer S. Frank, Northridge, Calif.

[73] Assignee: Aquality, Inc., Chatsworth, Calif.

[22] Filed: Aug. 25, 1975

[21] Appl. No.: 607,282

Related U.S. Application Data

[63] Continuation-in-part of Ser. No. 428,421, Dec. 26, 1973, abandoned.

[52] U.S. Cl. ............................. 356/182; 356/184; 356/188; 356/246
[51] Int. Cl.² ..................................... G01J 3/48
[58] Field of Search .......... 356/180, 182, 184–186, 356/188, 189, 192, 194, 201, 246; 350/315, 318

[56] References Cited
UNITED STATES PATENTS

| | | | |
|---|---|---|---|
| 1,976,672 | 10/1934 | Peet | 356/182 |
| 3,176,577 | 4/1965 | Frank | 356/182 |
| 3,718,439 | 2/1973 | Rosse et al. | 356/246 |
| 3,837,745 | 9/1974 | Acker et al. | 356/201 |

FOREIGN PATENTS OR APPLICATIONS

| | | | |
|---|---|---|---|
| 699,181 | 11/1953 | United Kingdom | 356/185 |

*Primary Examiner*—John K. Corbin
*Assistant Examiner*—F. L. Evans
*Attorney, Agent, or Firm*—Robert E. Geauque

[57] ABSTRACT

A visual color comparator for testing the condition of a liquid and utilizing dual liquid dip cells which are integrally connected together so that identical sample quantities of a liquid can be obtained by dipping the dual cells into the liquid, and a mounting for the color standards which provide for easy change of color standards when the test is changed.

8 Claims, 9 Drawing Figures

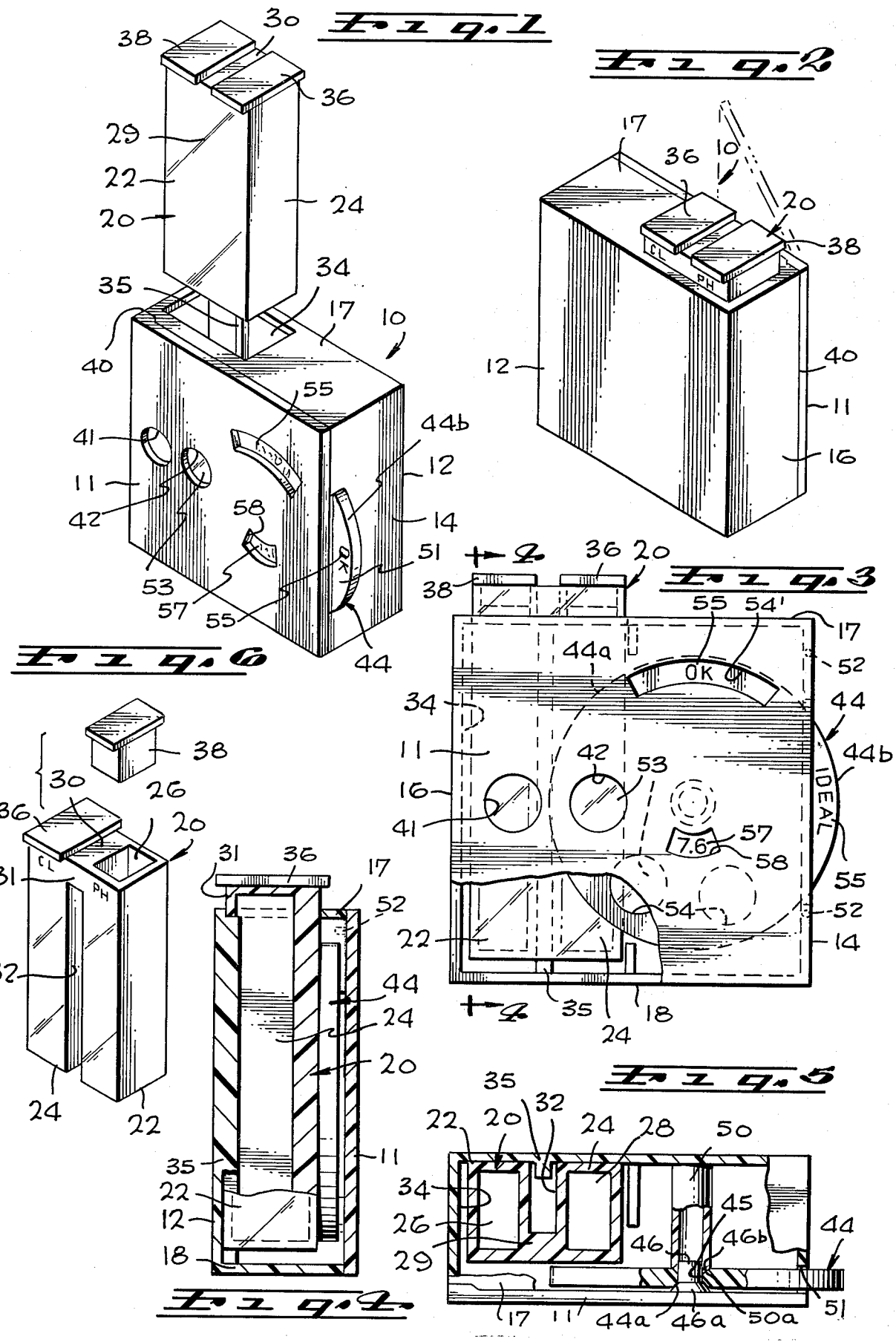

VISUAL COLOR COMPARATOR WITH INTEGRAL DUAL DIP CELLS

BACKGROUND OF THE INVENTION

This application is a Continuation-In-Part of U.S. application Ser. No. 428,421 filed Dec. 26, 1973 by Gomer S. Frank, now abandoned.

It is common practice to determine the condition of a liquid, such as water, by treating a sample of the liquid with a chemical indicator reagent which varies its color in accordance with its condition and thereafter comparing the resulting color with color standards to obtain an indication of the condition of the liquid. By comparing the color of treated swimming pool water with graduated standard colors of known values, the chlorine and pH values of the water may be easily determined and at the same time, the required chemical additive can be indicated to maintain the water in ideal condition. Such a device is disclosed in U.S. Pat. No. 3,176,577 issued Apr. 6, 1965 to the present inventor.

Each of the color standards can be fabricated from a layer of colored plastic and the individual standards are movable one at a time into position opposite the sample of treated water for color comparison. When swimming pool water is being tested for chlorine, a sample of the water is treated with a predetermined quantity of a reagent solution, such as Ortho-tolidin, to obtain a test color. A test color for water pH is obtained by treating the water sample with a suitable pH reagent, such as phenol-red.

In some devices, the color standards are placed over an untreated quantity of the same water being tested so that the natural color of the water will combine with the color of the individual standards to compensate each color standard with the natural water color. Since the resulting color of the water sample treated with the reagent will also vary with the natural color of the water, a more exact color comparison can be obtained.

SUMMARY OF THE INVENTION

It has been determined that the natural color of water taken from a body of water at different locations can vary widely. Thus, if the water sample used for compensation of the color standards is taken from a different location in the body of water than which the treated test sample is taken, the different natural colors of the two water samples will result in an inexact color comparison. In order words, the color standards are being compensated by natural water of different color than that of the test sample.

The present invention provides for a more exact color comparison by assuring that the quantity of water which is used to compensate the color standards is taken from exactly the same location as the sample of water which is to be treated with the indicator color reagent. A dual dip cell is utilized to collect both the comparison sample and the color test sample at the same time from precisely the same location in the body of water. This results from having two cells integrally connected together. The two dip cells are spaced slightly apart by a connecting panel connecting between the front sides of the two cells so that a slot exists between the two cells. To assure that the cells are properly located within the container for the cells, the container has a ridge which projects from the inside back surface and enters the slot. One of the cells is located by the ridge behind an opening in the front side of the container over which passes the individual color standards, one at a time. Therefore, the natural untreated water placed in this cell will modify each color standard when it appears at the opening. The other cell contains water for treatment with a reagent and this cell is placed behind a second opening in the container adjacent the first opening so that the color of the treated test water sample can be easily compared with the individual color standards. When the dual cells are dipped into a body of water, the two water samples are obtained at the same time and from the same location so that the samples are identical and have the same natural color.

In one form of the invention the dip cells are inserted through a top aperture in the container so that the cells are viewed through the two openings in a plane transverse to the cells. In another form of the invention, the bottom end of the dip cells are inserted through another aperture in the back side of the container so that the cells are viewed through the two openings in a plane passing lengthwise of the cells. Therefore, the light passes through a greater length of liquid in the dip cells to produce more exact liquid color observed at the two openings.

The front panel of the container for the cells also contains two slots which display different information concerning the condition of the water and instructions for the required treatment to put the water in a desired condition. This information is carried at two different radii on the rotating disc which also carries the individual color standards at an intermediate radius. A separate indicator disc is available for each test which is to be conducted, since only one test at a time can be conducted with a dual dip cell.

The present invention also provides a simple structure for mounting an indicator disc having an opening at its center. A post extends inwardly from the front panel of the container through the opening of the disc and further extends into the end opening in a cylindrical projection from the back panel of the container. The front panel is hinged to a side of the container so that a disc may be inserted into the container and the front panel closed, thereby projecting the post through the hole in the disc and into the opening in the cylinder. Thereafter, a small portion of the edge of the disc projects through a side panel so that the disc can be rotated with the fingers to move individual color standards past the first opening in the front panel.

BRIEF DESCRIPTION OF THE DRAWINGS

FIG. 1 is an expanded perspective view of the container and dual dip cells of the color comparator of the present invention;

FIG. 2 is a perspective view of the color comparator with the dual dip cells located in the container;

FIG. 3 is a front elevational view of the color comparator with a portion broken away;

FIG. 4 is a vertical section along line 4—4 of FIG. 3;

FIG. 5 is a top plan view with the dual dip cells shown in section;

FIG. 6 is an expanded perspective view of the dual dip cells with one cell cap removed;

DESCRIPTION OF THE PREFERRED EMBODIMENT

Figure 7:
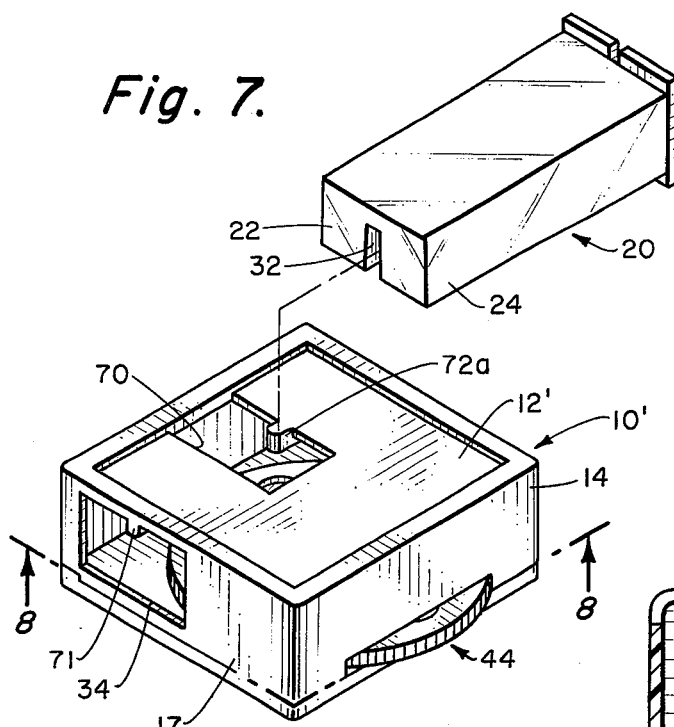
FIG. 7 is an expanded perspective of a modification of the subject invention wherein the dip cells are inserted endwise into the container.

The embodiment of this invention chosen for illustration consists of a compartment 10 having a front panel 11, back panels 12, side panels 14 and 16, top panel 17 and bottom panel 18. The compartment is fabricated of an opaque plastic material so that the interior can be observed only through opening in the compartment. Dual dip cells 20 comprises two rectangular shaped cells 22 and 24 which have interior spaces 26 and 28, respectively. The cells are spaced apart by a partition 29 connecting at the front panels of the cells and by a partition 30 extending between the tops of the cells with a slight extension 31 down the back of the cells. A groove 32 exists between adjacent sides of the cells and is open at the back of the cells. The top panel 17 of the compartment 10 contains a rectangular opening or aperture 34 into which the dual cells 10 can be inserted into the container.

A ridge 35 projects from the interior side of back panel 12 at a location midway of opening 17 and extends substantially the entire height of the back panel. When the dual cells 20 are inserted into aperture 34 the groove 32 receives the ridge 35 and the cells are guided into the compartment by the ridge until the top partition extension 31 engages the top of the ridge, the bottom of the cells being spaced slightly from the bottom panel 18. The interior spaces in cells 22 and 24 can be closed by caps 26 and 38, respectively.

The front panel 11 is hinged to side panel 16 along the hinge line 40 and the hinge can consist of a thin connecting layer of plastic or of standard plastic hinges. By pivoting the front panel, access is obtained into the interior of compartment 10. Two circular openings 41 and 42 in front panel 11 are located adjacent one another with opening 41 overlying cell 22 and opening 42 overlying cell 24 when the dual cells are inserted into the container, as above described and as illustrated in FIG. 3. An edge portion 44a of an indicating disc 44 is located between opening 42 and the front of cell 24. The disc 44 has a central opening 45 which receives a post 46 connected to the front panel by a tapered portion 46a. The disc opening has a corresponding tapered section 44c so that the disc is centered when the post is inserted into disc opening 45. A cylindrical hollow projection 50 extends from the back panel 12 and is axially aligned with post 46 to receive the end of post 46 when front panel is closed. The end of projection 50 is tapered at 50a to receive the inside taper surface 44d of the disc 44. It is therefore apparent that disc 44 is retained for rotation on post 46 between the tapered surfaces 46a and 50a when the front panel is closed. A portion 44b of disc 44 extends through a slot 51 in side panel 14 so that the disc can be rotated by the fingers while the front panel is closed. A standard snap fastener 52 having portions on both side 14 and front panel 11 can be utilized to hold front panel 11 in the closed position shown in FIG. 1.

The disc 44 contains a plurality of circular color standards 53 in the form of discs located in disc opening 54 of the same size as opening 42. The standards are spaced around the disc 44 on the same radius. As the disc 44 is rotated, one after another of the different colored discs 53 are viewable through the front panel opening 42. A series of different directions or condition indicators 55 are located around the circumference of disc 44. These instructions 55 are displayed, one at a time, through a slit opening 54' in the front panel and each visual instruction corresponds to a particular color standard then opposite the opening 42. Also, a series of pH number 57 are spaced around the disc 44 on a smaller radius than the color standard discs 53. A different pH number can be observed through slit opening 58 in the front panel for each separate color disc located at opening 42.

The disc 44 can consist of two pieces of plastic laminated together after the individual color discs 52 are placed between the pieces at the disc openings 54. The disc 44 carries markings 55 and 57 on its surface which corresponds to the particular test being conducted. For instance, if the water is being tested for chlorine content, the subject matter 55 and 57 would be different than if the water is being tested for pH. The discs 44 are easily exchangeable by simply opening the front panel 11, removing one disc from post 46 and substituting another disc on the post and closing panel 11 so that new disc is now retained between front panel 11 and the end of cylindrical projection 50.

In utilization of the color comparator, the dual dip cells 20 is removed from compartment 10 and dipped into the body of water to be tested until both cells 22 and 24 are filled. The dip cell is then replaced in compartment 10 by inserting ridge 35 into groove 32. The predetermined amount of reagent is added to the water in cell 22 so that a color will be developed corresponding to the particular condition of the water being tested. This color is visible through opening 41. The disc 44 is then rotated until a color standard disc 53 of the same color as the water test sample appears in opening 42 opposite opening 41. It is then possible to read the condition or instruction at slits 54' and 58. If another condition of the water is to be tested next, the cells are emptied and cleaned and a new disc 44 is substituted on post 46 and the front panel again closed.

Figure 8:
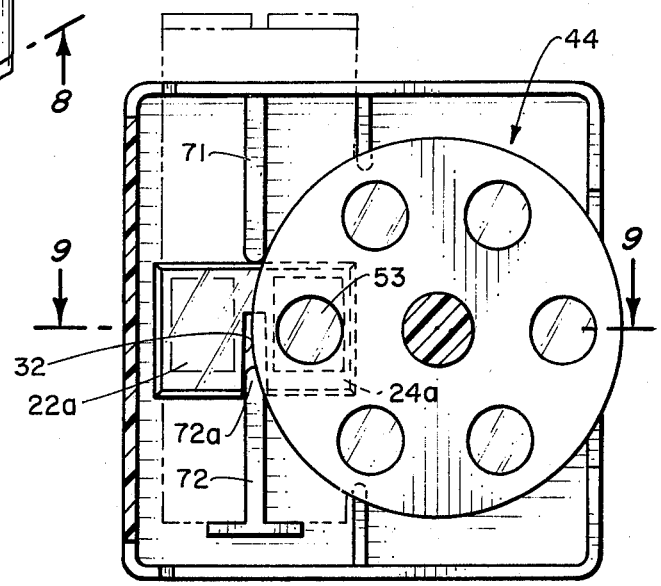
FIG. 8 is a vertical section along line 8—8 of FIG. 7 showing the ends of the dip cells and the colored discs.
Figure 9:
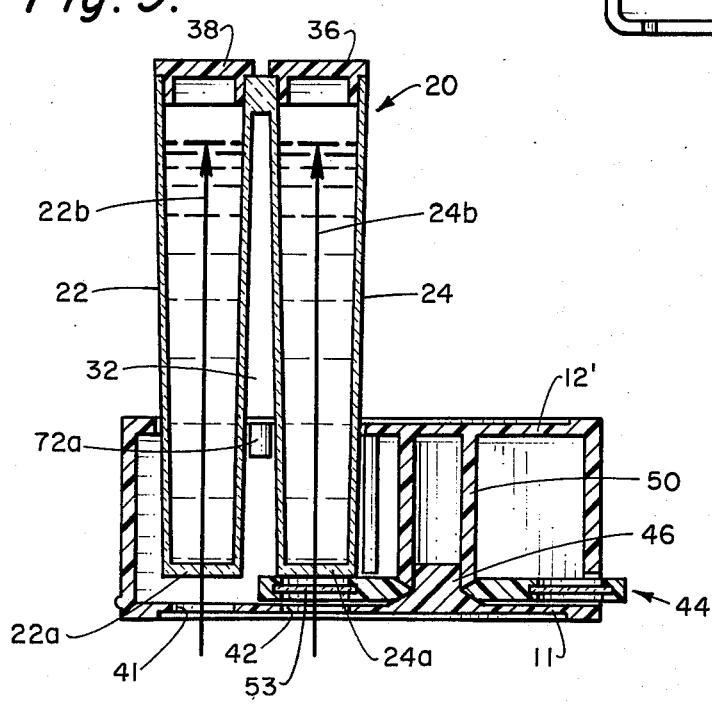
FIG. 9 is a transverse section long line 9—9 of FIG. 8 showing the line of view through the compartment into the ends of the dip cells.

A modification is illustrated in FIGS. 7–9 and consists of a compartment 10' which is constructed the same as compartment 10 of the prior embodiment with the exception that an aperture 70 is cut in back panel 12'. The presence of this aperture removes a portion of ridge 35 so that two separate ridges 71 and 72 project inwardly from back panel 12'. The ridge 72 projects into the aperture 70 to provide a guide portion 72a which has a thickness to snugly receive the groove 32 between the dip cells 22 and 24. When the ends of the dip cells 20 are inserted into the aperture 70, end 24a of cell 24 is opposite a colored disc 53 in disc 44 which, in turn, is opposite the opening 42 in front panel 11 and the end 22a of cell 22 is opposite the opening 41, see FIG. 9. In this position, the circumference of the dip cells 20 snugly fits the edges defining aperture 70 and the insertion of the dip cells is guided by projection 72a located in groove 32.

As in the prior embodiment, the disc 44 is rotatably mounted on post 46 to successively place place one colored disc 53 after another between the cell end 24a and the opening 42. The length of light penetration through the liquid in cells 22 and 24 is illustrated by the length of sight lines 22b and 24b, respectively. It is therefore apparent that the light leaving the ends of the dip cells will correspond more nearly to the liquid color in the cells because of the further distance the light travels through the liquid. Thus, a more exact comparison can be obtained between the color of the treated liquid in cell 22 and the color of the disc 53 showing in opening 42 opposite cell 24. The caps 36 and 38 are sufficiently liquid tight to permit the dip cell to be placed horizontally through aperture 70 without leakage. The opening 34 is also present in top panel 17 so that the modification can be utilized as the prior embodiment by inserting the dip cell through the top opening as illustrated in the phantom line position of the dip cells in FIG. 8. The interrupted ridge portions 71 and 72 are of sufficient length to guide the dip cells in the same manner as ridge 35.

Because the dual cells are integrally connected together, the water dipped into each cell is the same in natural color and chemical composition. The color developed in the test sample cell 22 will be influenced by the color of the natural water. Also, in placing the individual color standards over cell 24 containing only natural water, the color standards will be compensated for natural color in the same manner. Thus, a true comparison can be obtained between the color of the tested sample and the color of the standard. Also, the plastic material of the dual cells is identical so that any color effect of the plastic material will be compensated for since the same plastic material is opposite both openings 44 and 42. While the use of the invention has been discussed in connection with testing swimming pool water, it can be utilized to test liquids other than water with varying natural colors since compensation of natural color is always present.

What is claimed is:

1. A visual color comparator for testing a property of a liquid comprising:
    first and second dip cells;
    means for rigidly connecting said cells together in side by side location with a space therebetween;
    a housing compartment for said cells;
    an aperture in said compartment through which said cells are inserted together after being simultaneously dipped into said liquid to fill said cells;
    guide means on said compartment and inserted into said space to guide the movement of said cells;
    said compartment having a front panel opposite said cells containing first and second openings opposite said first and second cells, respectively, after insertion of said cells;
    a plurality of different color standards movable one at a time into position between said second cell and said second opening;
    said first cell receiving a reagent which colors the liquid in said cell and said color standards being moved until a standard matches the liquid color.

2. A visual color comparator as defined in claim 1 having a disc located within said compartment and having a portion positioned between said second cell and said second opening;
    means for rotatably mounting said disc for rotation within said housing;
    said color standards comprising individual material portions of varying color located in openings in said disc and spaced around a radius of said disc so as to pass, opposite said second opening as said disc rotates.

3. A visual color comparator as defined in claim 2 wherein:
    said compartment having a back panel;
    said mounting means comprising a post extending inwardly from said front panel and a hollow member coaxial with said post and projecting inwardly from said back panel, said front panel being movable between open and closed positions to provide access to said mounting means, a central opening in said disc for passage of said post, the end of said post extending into said hollow member when said front panel is in closed position and said disc is mounted on said post.

4. A visual color comparator as defined in claim 1;
    said compartment having a back panel containing said aperture, said guide means comprising a projection secured to said back panel and extending into said aperture, said projection being inserted into said space to guide endwise insertion of said cells, said first and second openings in said front panel being opposite the ends of said first and second dip cells after insertion of said cells, said color standards being movable past the end of said second cell and said second opening.

5. A visual color comparator for testing a property of a liquid comprising:
    first and second dip cells;
    means for rigidly connecting said cells together in side by side location;
    a housing compartment for said cells;
    an opening in said compartment through which said cells are vertically inserted together after being simultaneously dipped into said liquid to fill said cells;
    said compartment having a front panel opposite said cells containing first and second openings opposite said first and second cells, respectively;
    a plurality of different color standards movable one at a time into position between said second cell and said second opening;
    said first cell receiving a reagent which colors the liquid in said cell and said color standards being moved until a standard matches the liquid color;
    said connecting means spacing said cells apart to provide a vertical space therebetween;
    said compartment having a back panel with a vertical ridge projecting therefrom;
    said ridge entering said space and guiding said cells while being vertically inserted into said compartment.

6. A visual color comparator as defined in claim 5 wherein:
    said cells are each rectangular in shape, said connecting means comprises a partition extending between said cells in the plane containing the front of each cell.

7. A visual color comparator as defined in claim 5 having stop means located in said space to limit the insertion of said cells into said compartment.

8. In a visual color comparator having dual liquid dip cells located between front and back panels of a compartment, one of said cells receiving a coloring reagent and the other being located behind different color standards supported on a rotating disc, the improvement comprising mounting means for rotatably mounting said disc within said compartment, said mounting means comprising a post extending inwardly from said front panel and a hollow member coaxial with said post and projecting inwardly from said back panel, said front panel being movable between open and closed positions to provide access to said mounting means, a central opening in said disc for passage of said post and smaller than said hollow member, the end of said post extending into said hollow member when said front panel is in closed position and said disc is mounted on said post.

* * * * *